US006878699B1

(12) United States Patent
Hemscheidt et al.

(10) Patent No.: US 6,878,699 B1
(45) Date of Patent: Apr. 12, 2005

(54) TACCALONOLIDE MICROTUBULE STABILIZING AGENTS

(75) Inventors: Thomas K. Hemscheidt, Honolulu, HI (US); Susan L. Mooberry, San Antonio, TX (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/979,447

(22) PCT Filed: May 18, 2000

(86) PCT No.: PCT/US00/13795

§ 371 (c)(1),
(2), (4) Date: Apr. 29, 2000

(87) PCT Pub. No.: WO00/71563

PCT Pub. Date: Nov. 30, 2000

Related U.S. Application Data
(60) Provisional application No. 60/193,649, filed on Mar. 31, 2000, and provisional application No. 60/135,409, filed on May 21, 1999.

(51) Int. Cl.⁷ .................. A61K 31/56; A61K 31/58; A61K 31/585
(52) U.S. Cl. .................. 514/177; 514/172; 514/175; 514/182
(58) Field of Search ................. 514/172, 175, 514/177, 182

(56) References Cited

U.S. PATENT DOCUMENTS 5,824,701 A * 10/1998 Greenwald et al. ......... 514/449
2002/0094991 A1 * 7/2002 Gallaher ..................... 514/283

FOREIGN PATENT DOCUMENTS

WO    WO 01 40256    6/2001

OTHER PUBLICATIONS

Rouhi "A synthetic tour de force" Chemical & Enginerring News, vol. 79, No. 49, p. 9.*
Chen et al., "Bitter principles from Tacca plants—structures of taccalonolide A and B," CHEMABS, XP–002163016.
Vasanth et al., Plant Anti–Malarial Agents, Journal of Scientific and Industrial Research, vol. 49, No. 2, 1990, p. 68–77. XP–001014380.

(Continued)

*Primary Examiner*—Shengjun Wang
(74) *Attorney, Agent, or Firm*—Stephen E. Reiter; Foley & Lardner LLP

(57) ABSTRACT

In accordance with the present invention, there have been identified extracts from a tropical plant that initiate paclitaxel-like microtubule bundling. Bioassay-directed purification yields the steroid taccalonolide A. Taccalonolide, like paclitaxel, initiates the formation of abnormal interphaes and mitotic microtubules. Cells treated with taccalonolide exhibit thick bundles of microtubules that appear to nucleate independent of the microtubule organizing center. Abnormal mitotic spindles consisting of multipolar spindles are initiated by taccalonolide and resemble abnormal mitotic spindles found in the presence of paclitaxel. Like paclitaxel, taccalonolide causes the breakdown of the nucleus into micronuclei. Taccalonolide causes G2/M arrest, Bcl-2 phosphorylation and initiates an apoptotic cascade that includes the activation of caspase 3. Taccalonolide is an effective inhibitor of proliferation against both SK-OV-3 and MDA-MB-435 cell with $IC_{50}$ values of 2.3 $\mu$M and 2.1 $\mu$M respectively. In contrast to paclitaxel, taccalonolide is effective against the multidrug resistant SKVLB-1 cellline and thus appears to be a poor substrate for P-glycoprotein-mediated transport. Although taccalonolide is almost equipotent with paclitaxel in its effects on cellular microtubules, it is much less potent than paclitaxel in its ability to initiate the polymerization of purified tubulin and microtubule protein. Taccalonolide A is the first microtubule stabilizing agent to be discovered from a plant since identification of the mechanism of action of paclitaxel and it is the first natural product steroid identified to have these cellular effects.

19 Claims, 7 Drawing Sheets

OTHER PUBLICATIONS

Scheuer, "From the rain forest to the reef—searching for bioactive natural products in the mid–Pacific," Medicinal Research Reviews, vol. 14, No. 5, p. 487–503. XP–001014442.

Chen Degui, "Chinese herbal medicine tablet for treating cancer," Dec. 14, 1994. XP–002173411.

Chen et al., "Five Taccalonolides from Tacca Plantaginea," Planta Medica, vol. 63, No. 1, 1997, p. 40–43. XP–000990396.

Shen et al., "Taccalonolides from Tacca Plantaginea," Phytochemistry, vol. 42, No. 3, 1996, p. 891–893. XP–000990423.

Shen et al., "The Pentacyclic Steroidal Constituents of Tacca Plantaginea: Taccalonolide E and F," Chinese Journal of Chemistry, vol. 9, No. 1, 1991, p. 92–94. XP000990402.

* cited by examiner

Bcl-2 phosphorylation

Control    4 hr    8 hr    18 hr    24 hr

TACCALONOLIDE MICROTUBULE STABILIZING AGENTS

RELATED APPLICATIONS

This application is a 371 of PCT International Application No. PCT/US00/13795, filed May 18, 2000, which claims benefit of U.S. application Ser. No. 60/135,049, filed May 21, 1999 and U.S. application Ser. No. 60/193,649, filed Mar. 31, 2000.

This invention was made with United States Government support under Grant No. DAMD17-97-17212 awarded by the Department of Defense. The Government has certain rights to the invention.

FIELD OF INVENTION

The present invention relates to methods for inhibiting cell proliferation and compounds useful therefor.

BACKGROUND OF THE INVENTION

Neoplastic diseases or cancers, characterized by the proliferation of cells not subject to normal growth regulation, are a major cause of death in humans. An estimated 1,221,800 new cases and 561,000 deaths are expected to occur in 1999. Lung cancer remains the leading cause of cancer-related deaths in the United States; the estimated 158,900 deaths would account for 28% of the total.

Clinical experience in chemotherapy has demonstrated that new and more effective cytotoxic drugs are desirable to treat these diseases. Such experience has also demonstrated that drugs which disrupt the microtubule system of the cytoskeleton can be effective in inhibiting the proliferation of neoplastic cells.

The microtubule system of eucaryotic cells is a major component of the cytoskeleton and is in a dynamic state of assembly and disassembly; that is, heterodimers of tubulin are polymerized to form microtubules, and microtubules are depolymerized to their constituent components. Microtubules play a key role in the regulation of cell architecture, metabolismn, and division, and the dynamic state of the microtubules is critical to their normal function. With respect to cell division, tubulin is polymerized into microtubules that form the mitotic spindles. The microtubules are then depolymerized when the mitotic spindle's role has been fulfilled. Accordingly, agents which disrupt the polymerization or depolymerization of microtubules, and thereby inhibit cell growth, comprise some of the most effective chemotherapeutic agents in clinical use.

Such anti-mitotic agents or poisons all kinetically inhibit the normal dynamics of microtubules. There are subtle differences between certain classes of antimicrotubule agents based on their molecular mechanism of action Colchicine binds to soluble tubulin and then is incorporated into a growing microtubule, vinblastine binds to the microtubule end and thereby suppresses microtubule dynamics. At high concentrations, both colchicine and vinblastine cause the loss of cellular microtubules. Paclitaxel and related taxanes also inhibit microtubule dynamics, yet at high concentrations these agents cause an increase in polymerized tubulin in the cell and thick microtubule bundles are formed.

Paclitaxel was first isolated in 1971 in the bark of the Pacific yew tree (*Taxus brevifolia*), and was approved in 1992 by the US Food and Drug Administration for treatment of metastatic ovarian cancer and later for breast cancer. Paclitaxel has attracted unusually strong scientific attention, not only because of its unique antiproliferative mechanism of action, but also because it is active against a broad range of tumors. The discovery of the effectiveness of the natural product paclitaxel lead to the production and testing of semisynthetic congeners including docitaxel (Taxotere). These compounds, taxanes, are now recognized as a new class of anticancer compounds.

One drawback of paclitaxel is its extreme insolubility: Paclitaxel can be administered effectively only in a solvent including cremophor (the commercially available formulation marketed as Taxol), which combination can provoke severe hypersensitive immune responses. As a result of these drawbacks, it is considered desirable to explore the use of other naturally-occurring compounds with similar modes of action In addition, merely having activity as an antimitotic agent does not guarantee efficacy against a tumor cell, and certainly not a tumor cell which exhibits a drug-resistant phenotype. Vinca alkaloids, such as vinblastine and vincristine, and taxanes are effective against neoplastic cells and tumors, yet they lack or display reduced activity against drug-resistant tumors and cells. One basis for a neoplastic cell displaying drug resistance (DR) or multiple-drug resistance (MDR) is through the over-expression of P-glycoprotein. Compounds which are poor substrates for transport by P-glycoprotein should be useful in circumventing such DR or MDR phenotypes.

Accordingly, the exhibition of the DR or MDR phenotype by many tumor cells and the clinically proven mode of action of anti-microtubule agents against neoplastic cells necessitates the development of anti-microtubule agents cytotoxic to non-drug resistant neoplastic cells as well as cytotoxic to neoplastic cells with a drug resistant phenotype.

Since the discovery of the mechanism of action of paclitaxel, only four other nontaxane chemical classes (epothilones A and B, discodermolide, eleutherobin and related sarcodictyins A and B, and laulimalides) have been identified that possess a similar mode of action. The epothilones were isolated from the myxobacterium *Sorangium cellulosum* as a result of a large-scale screening effort. The epothilones have generated significant interest, as they retain activity against drug-resistant cell lines.

Discodermolide was purified from the marine sponge *Discodemia dissoluta* as an immunosuppressant and was screened for antimitotic activity on the basis of a predictive structure-activity relationship when compared with other tubulin-interacting drugs. Discodermolide promotes tubulin assembly more potently than Taxol and it is an effective inhibitor of cell growth in paclitaxel-resistant cells.

Eleutherobin, a potent cytotoxin from the soft coral eleutherobia sp., promotes tubulin polymerization but exhibits cross-resistance to paclitaxel-resistant cell lines. The potential therapeutic usefulness of these new microtubule-stabilizing compounds, and whether they will provide advantages over the taxanes, have yet to be determined.

Epothilones have been isolated from a species of bacteria found in soil samples collected from the banks of the Zambesi River in the Republic of South Africa, and have been recently synthesized.

Laulimalides have been isolated from the marine sponge *C. myofijiensis*. Strong paclitaxel-like microtubule-stabilizing activity has been found in the laulimalides.

Accordingly, it remains desirable to identify additional compounds with modes of action similar to the taxanes, but which display different tissue specificity, solubility, and/or activity against drug-resistant, and particularly multiple-drug resistant, tumors and cells.

BRIEF DESCRIPTION OF THE INVENTION

In accordance with the present invention, there have been identified extracts from a tropical plant that initiate paclitaxel-like microtubule bundling. Bioassay-directed purification yields the steroid taccalonolide A. Taccalonolide, like paclitaxel, initiates the formation of abnormal interphase and mitotic microtubules. Cells treated with taccalonolide exhibit thick bundles of microtubules that appear to nucleate independent of the microtubule organizing center. Abnormal mitotic spindles consisting of multipolar spindles are initiated by taccalonolide and resemble abnormal mitotic spindles found in the presence of paclitaxel. Like paclitaxel, taccalonolide causes the breakdown of the nucleus into micronuclei. Taccalonolide causes G2/M arrest, Bcl-2 phosphorylation and initiates an apoptotic cascade that includes the activation of caspase 3.

Taccalonolide is an effective inhibitor of proliferation against both SK-OV-3 and MDA-MB435 cells with $IC_{50}$ values of 2.3 $\mu$M and 2.1 $\mu$M, respectively. In contrast to paclitaxel, taccalonolide is effective against the multidrug resistant SKVLB-1 cell line and thus appears to be a poor substrate for P-glycoprotein-mediated transport. Although taccalonolide is almost equipotent with paclitaxel in its effects on cellular microtubules, it is much less potent than paclitaxel in its ability to initiate the polymerization of purified tubulin and microtubule protein. Taccalonolide A is the first microtubule stabilizing agent to be discovered from a plant since the identification of the mechanism of action of paclitaxel and it is the first natural product steroid identified to have these cellular effects.

BRIEF DESCRIPTION OF TH FIGURES

Figures 3A, 3B:
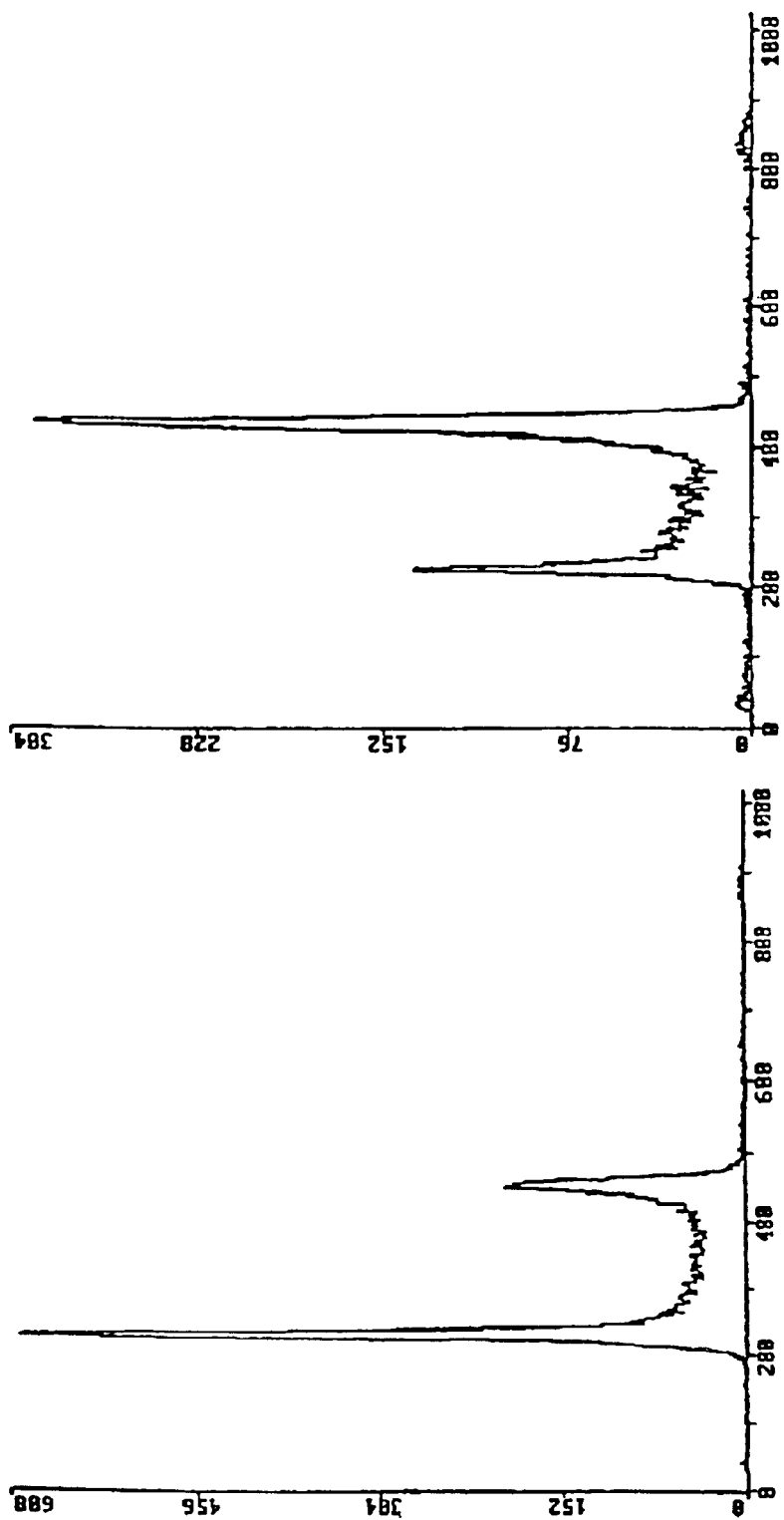
Figures 3C, 3D:
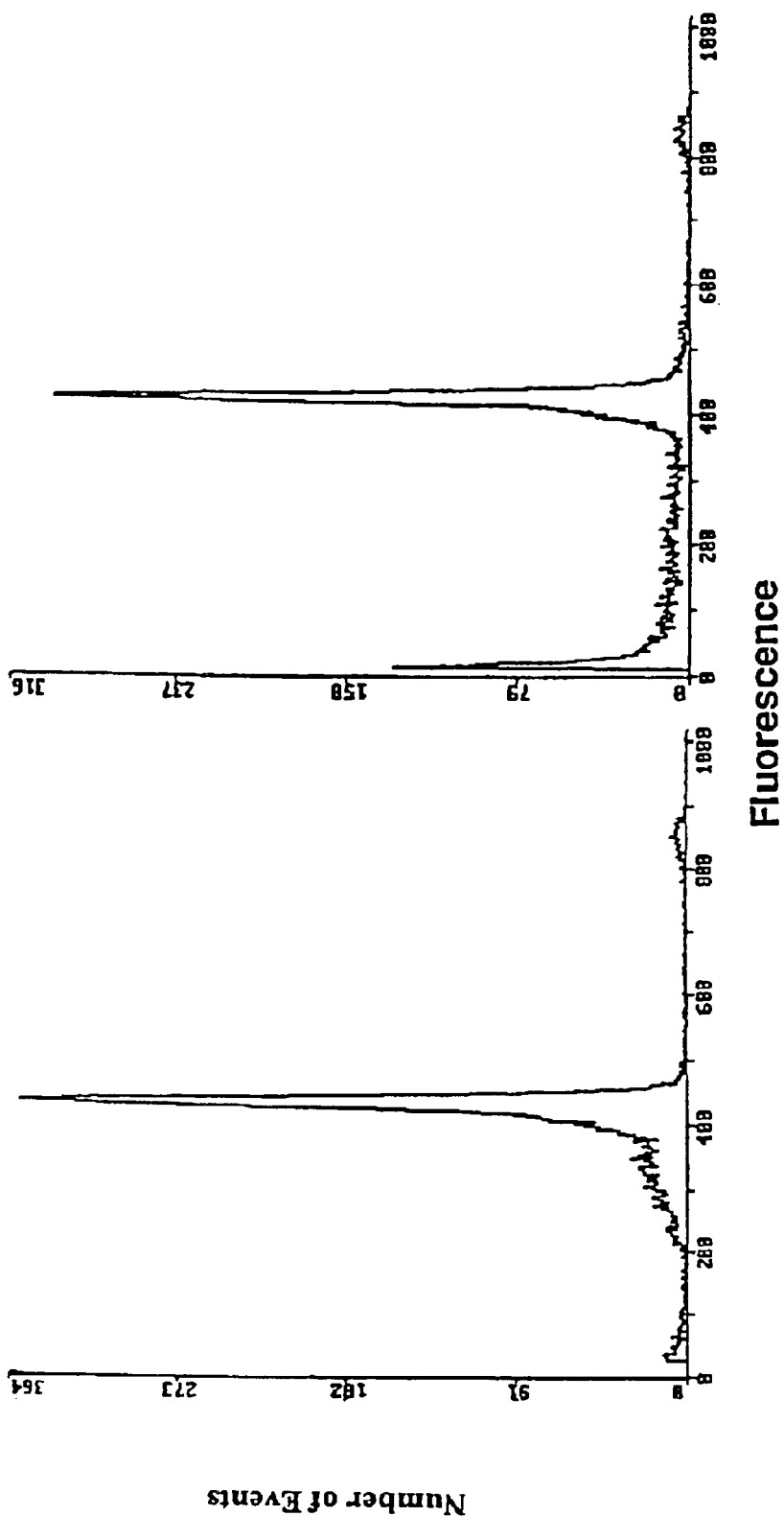

The several parts of FIG. 3 illustrate the cell cycle distribution of cells treated with taccalonolide. MDA-MB-435 cells in log phase growth were treated with vehicle (FIG. 3A) or 10 $\mu$m taccalonolide for 6 hr (FIG. 3B), 12 hr (FIG. 3C), or 24 hr (FIG. 3D) and then fixed, stained and analyzed by flow cytometry.

Figure 4:
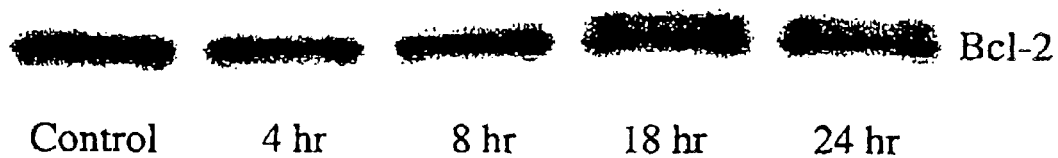

FIG. 4 shows the formation of the slower migrating form of Bcl-2 in cell lysates from cells treated with taccalonolide for the indicated times. The slower migrating form of Bcl-2 is caused by protein phosphorylation.

Figure 5:
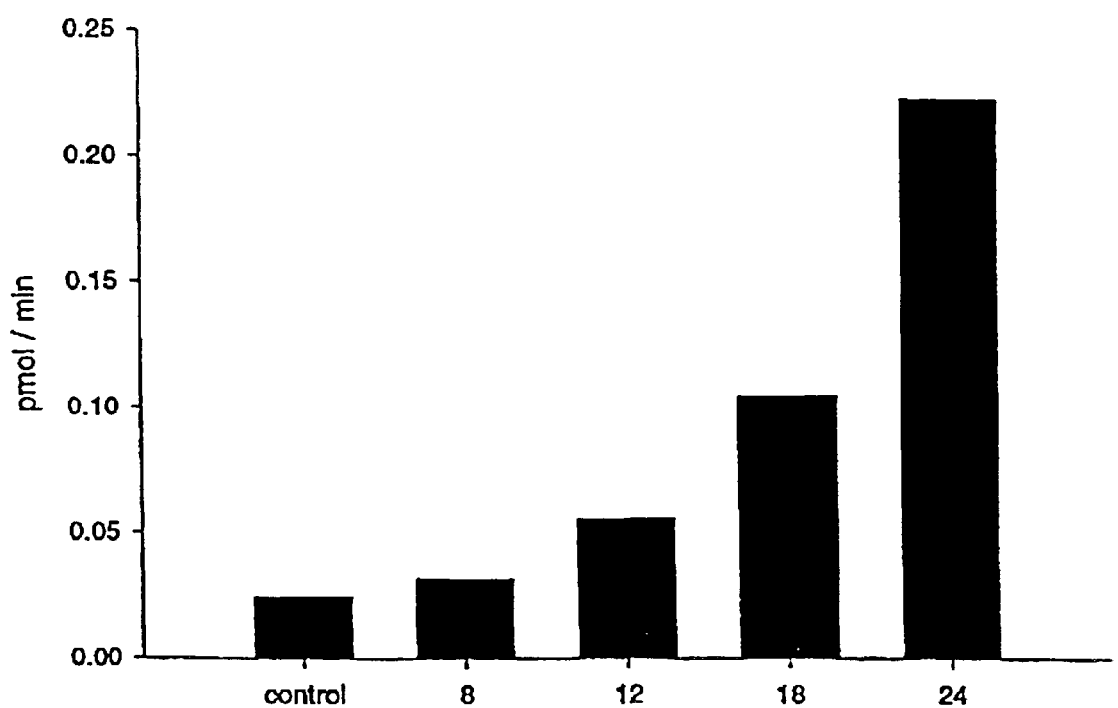

FIG. 5 illustrates caspase 3 activity of cell lysates prepared from taccalonolide-treated cells. Cell lysates (30 $\mu$g protein) were evaluated for the ability to cleave the caspase 3 substrate DEVD-pNA.

Figure 6:
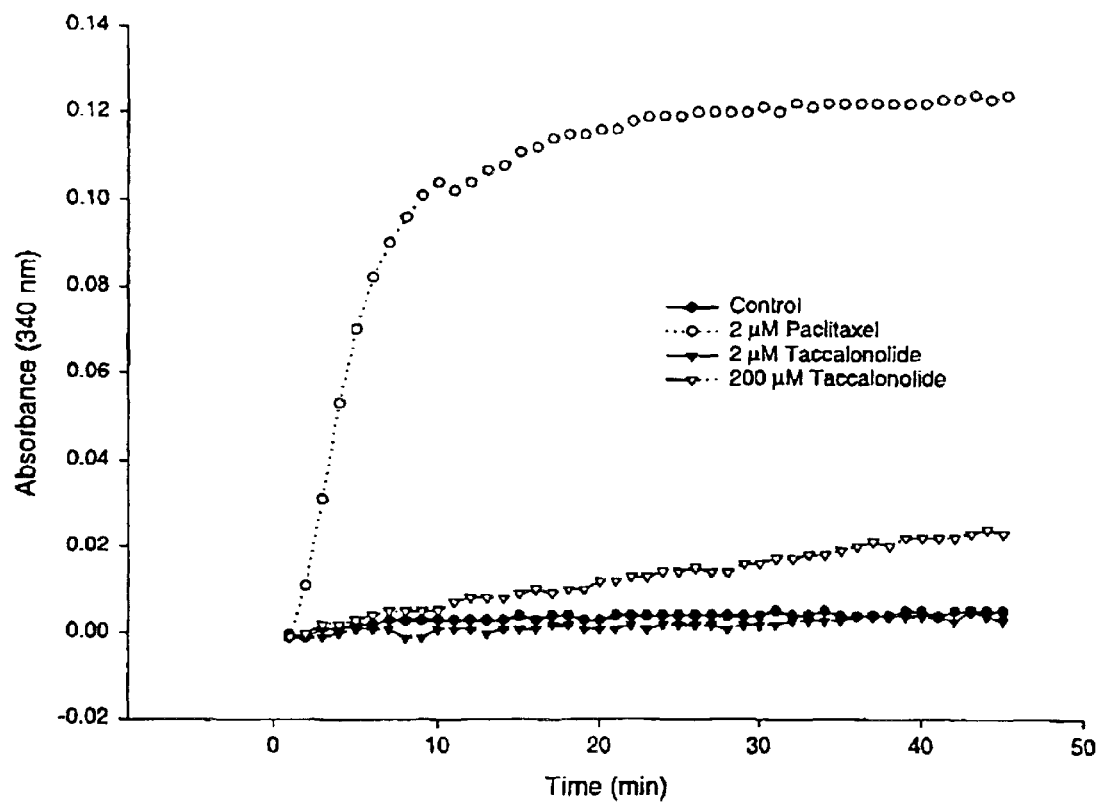

FIG. 6 illustrates the effect of taccalonolide on tubulin polymerization. The polymerization of purified, glycerol-free bovine brain tubulin was measured spectrophotometrically in a temperature-controlled (35° C.) microplate spectrophotometer in the presence of vehicle control (closed circles), 2 $\mu$M paclitaxel (open circles), or taccalonolide (2 $\mu$M-closed triangles; 200 $\mu$M-open triangles).

DETAILED DESCRIPTION OF THE INVENTION

In accordance with the present invention, there are provided methods of inhibiting the proliferation of a hyperproliferative mammalian cell having a multiple drug resistant phenotype, said method comprising contacting the cell with an amount of a taccalonolide compound effective to disrupt the dynamic state of microtubule polymerization and depolymerization to arrest cell mitosis, thereby inhibiting the proliferation of the cell. An additional feature of taccalonolide agents is that they stabilize microtubules and turn on a "cellular suicide" switch which leads to cancer cell death.

Taccalonolides contemplated for use in the practice of the present invention include compounds having the structure:

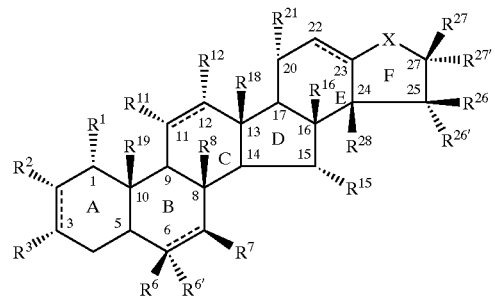

wherein:
R$^1$=H, lower alkyl, hydroxy, lower alkoxy or acyloxy,
R$^2$=H, OH, or R$^2$ and R$^3$ cooperate to form an epoxide at C-2/C-3,
R$^3$=H, OH, or R$^3$ cooperates with R$^2$ to form an epoxide at C-2/C-3,
R$^6$=H, OH, or a carbonyl oxygen if R$^{6'}$ is not present,
R$^{6'}$, when present, is H or OH,
R$^7$=H, lower alkyl, hydroxy, lower alkoxy or acyloxy,
R$^8$=H or lower alkyl,
R$^{11}$=H, lower alkyl, hydroxy, lower alkoxy or acyloxy,
R$^{12}$=H, lower alkyl, hydroxy, lower alkoxy or acyloxy,
R$^{15}$=H, lower alkyl, hydroxy, lower alkoxy or acyloxy,
R$^{16}$=H or lower alkyl,
R$^{18}$=H or lower alkyl,
R$^{19}$=H or lower alkyl,
R$^{21'}$=H or lower alkyl,
R$^{26}$=H, lower alkyl, hydroxy, lower alkoxy or acyloxy,
R$^{26'}$=H or lower alkyl,
R$^{27}$=H, OH, or a carbonyl oxygen if R$^{27'}$ is not present,
R$^{27'}$, when present, is H or OH, and
R$^{28}$=H or lower alkyl;
wherein the F ring is optionally present, and when present,
X=O, NR$^x$ or CR$^x_2$, wherein each R$^x$ is independently H or lower alkyl, or when the F ring is not present, the substituent at C23 is H, lower alkyl, hydroxy, lower alkoxy or acyloxy, and C24 is H, lower alkyl, hydroxy, lower alkoxy or acyloxy, and wherein the dashed lines between C2/C3, C6/C7, C11/C12 and C22/23 represent optional double bonds at each position.

As used herein, lower alkyl refers to straight or branched chain alkyl groups having 1 up to 6 carbon atoms. Examples include methyl, ethyl, propyl, isopropyl, butyl, sec-butyl, isobutyl, t-butyl, and the like.

As used herein, lower alkoxy refers to oxygen-substituted alkyl radicals having 1–6 carbon atoms.

As used herein, acyloxy refers to the moiety —O—C(O)—R, wherein R is an alkyl radical having 1–6 carbon atoms, optionally hydroxy and/or amino substituted, e.g., methyl, ethyl, propyl, aminomethyl, hydroxymethyl, and the like.

Presently preferred taccalonolide compounds contemplated for use in the practice of the present invention include taccalonolide A, B and D, i.e., compounds according to the steroid structure set forth above wherein:

$R^1$ is —O-acetyl,
$R^2$ and $R^3$ cooperate to form an epoxide,
$R^6$ is a carbonyl oxygen and $R^{6'}$ is not present,
$R^7$ is hydroxy,
$R^8$ is H,
$R^{11}$ is —O-acetyl,
$R^{12}$ is —O-acetyl,
$R^{15}$ is —O-acetyl,
$R^{16}$ is H,
$R^{18}$ is methyl,
$R^{19}$ is methyl,
$R^{21}$ is methyl,
$R^{26}$ is methyl,
$R^{26'}$ is methyl,
$R^{27}$ is a carbonyl oxygen and $R^{27'}$ is not present,
$R^{28}$ is methyl,
X is O, and
there is a double bond between C22 and C23; (i.e., taccalonolide A); or $R^1$ is —O-acetyl,
$R^2$ and $R^3$ cooperate to form an epoxide,
$R^6$ is a carbonyl oxygen and $R^{6'}$ is not present,
$R^7$ is hydroxy,
$R^8$ is H,
$R^{11}$ is —O-acetyl,
$R^{12}$ is —O-acetyl,
$R^{15}$ is hydroxy,
$R^{16}$ is H,
$R^{18}$ is methyl,
$R^{19}$ is methyl,
$R^{21}$ is methyl,
$R^{26}$ is hydroxy,
$R^{26'}$ is methyl,
$R^{27}$ is a carbonyl oxygen and $R^{27'}$ is not present,
$R^{28}$ is methyl,
X is O, and
there is a double bond between C22 and C23 (i.e., taccalonolide B); or $R^1$ is —O-acetyl,
$R^2$ and $R^3$ cooperate to form an epoxide,
$R^6$ is a carbonyl oxygen and $R^{6'}$ is not present,
$R^7$ is —O-acetyl,
$R^8$ is H,
$R^{11}$ is —O-acetyl,
$R^{12}$ is —O-acetyl,
$R^{15}$ is hydroxy
$R^{16}$ is H,
$R^{18}$ is methyl,
$R^{19}$ is methyl,
$R^{21}$ is methyl,
$R^{26}$ is hydroxy,
$R^{26'}$ is methyl,
$R^{27}$ is a carbonyl oxygen and $R^{27'}$ is not present,
$R^{28}$ is methyl,
X is O, and
there is a double bond between C22 and C23 (i.e., taccalonolide D).

In addition, variants are known to exist in the basic taccalonolide structure, including taccalonolide C. These variants differ structurally from taccalonolide A and D as follows:

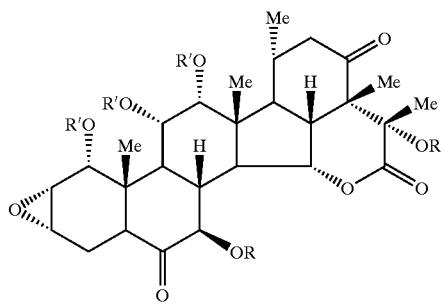

Certain of the taccalonolide compounds of the present invention were previously isolated from plants of the *Tacca* spp., herbaceous plants found in the Pacific region, and particularly from *Tacca plantaginea*, a plant found in China. More recently, the structures of a number of taccalonolides have been investigated, and taccalonolide A has been reported to display antimalarial and cytotoxic activity against p-388 leukemia in cell culture. The basis for this cytotoxic activity was not elucidated.

Taccalonolide A has also been isolated from *Tacca chantrieri* obtained in a to cultivated state. Lyophilized tubers were ground to a powder and extracted by stirring with dichloromethane/isopropanol for 24 hours at room temperature. The extraction was repeated under identical conditions with fresh solvent, and the combined extracts were evaporated in vacuo below 40° C. The residue was dissolved in 90% (v/v) aqueous methanol and extracted three times with equal volumes of hexanes, and hexane fractions were discarded. The aqueous methanol phase was diluted with water to 80% (v/v) aqueous methanol and extracted three times with equal volumes of toluene. The combined toluene fractions were evaporated in vacuo below 40° C. to dryness. The residue was dissolved in a minimum amount of dichloromethane and applied to a silica gel column equilibrated in ether, and the column was eluted with ether. Active fractions were combined and rechromatographed over silica gel using a solvent system of 75% methyl-tert-butyl ether/25% hexanes (v/v) containing 1% isopropanol.

The chemical structure of the taccalonolides as a class is amenable to chemical synthesis and the production of analogs, by techniques known in the art. For example, the structure for taccalonolides A, B and D referred to above includes a methyl group attached to carbon 24, which is structurally unusual for steroids. Thus, in one aspect of the present invention, taccalonolide analogs which do not include this unusual methyl group, while preserving the activity of the class of compounds, are also contemplated. Thus, novel taccalonolide analogs having the following structure are also considered to be within the scope of the present invention:

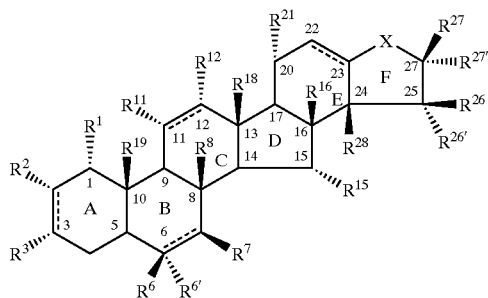

wherein:
R¹=H, lower alkyl, hydroxy, lower alkoxy or acyloxy,
R²=H, OH, or R² and R³ cooperate to form an epoxide at C-2/C-3,
R³=H, OH, or R³ cooperates with R² to form an epoxide at C-2/C-3,
R⁶=H, OH, or a carbonyl oxygen if R⁶' is not present,
R⁶', when present, is H or OH,
R⁷=H, lower alkyl, hydroxy, lower alkoxy or acyloxy,
R⁸=H or lower alkyl,
R¹¹=H, lower alkyl, hydroxy, lower alkoxy or acyloxy,
R¹²=H, lower alkyl, hydroxy, lower alkoxy or acyloxy,
R¹⁵=H, lower alkyl, hydroxy, lower alkoxy or acyloxy,
R¹⁶=H or lower alkyl,
R¹⁸=H or lower alkyl,
R¹⁹=H or lower alkyl,
R²¹=H or lower alkyl,
R²⁶=H, lower alkyl, hydroxy, lower alkoxy or acyloxy,
R²⁶'=H or lower alkyl,
R²⁷=H, OH, or a carbonyl oxygen if R²⁷' is not present, and
R²⁷', when present, is H or OH,
wherein the F ring is optionally present, and when present, X=O, NR$^x$ or CR$^x_2$, wherein each R$^x$ is independently H or lower alkyl, or when the F ring is not present, the substituent at
C23 is H, lower alkyl, hydroxy, lower alkoxy or acyloxy,
C24 is H, lower alkyl, hydroxy, lower alkoxy or acyloxy, and
wherein the dashed lines between C2/C3, C6/C7, C11/C12 and C22/23 represent optional double bonds at each position.

Taccalonolides contemplated for use in the practice of the present invention can be obtained from a variety of natural sources, or they can be prepared synthetically employing synthetic techniques known in the art.

In accordance with a further embodiment of the present invention, methods described herein can be carried out in the further presence of at least one additional anti-neoplastic agent. In further embodiments of the invention, cells subjected to invention methods are mammalian cells, including human cells.

The present invention also provides methods of alleviating a pathological condition caused by hyperproliferating, multiple drug resistant mammalian cells comprising administering to a subject in need thereof an effective amount of the pharmaceutical composition disclosed herein to inhibit proliferation of the cells. In further embodiments of the present invention, the mammalian cells are human.

In certain embodiments of the present invention, the method further comprises administering to the subject at least one additional therapy directed to alleviating the pathological condition. In certain embodiments of the present invention, the pathological condition is characterized by the formation of neoplasms. In further embodiments of the present invention, the neoplasms are mammary, small-cell lung, non-small-cell lung, colorectal, leukemia, melanoma, pancreatic adenocarcinoma, central nervous system (CNS), ovarian, prostate, sarcoma of soft tissue or bone, head and neck, gastric (which includes pancreatic and esophageal), stomach, myeloma, bladder, renal, neuroendocrine (which includes thyroid), non-Hodgkin's disease, Hodgkin's disease neoplasms, and the like.

The novel and the previously disclosed taccalonolide compounds contemplated for use in the practice of the present invention can be therapeutically employed as anti-neoplastic agents and thereby used in methods to treat neoplastic diseases. As used herein, "neoplastic" pertains to a neoplasm, which is an abnormal growth, such growth occurring because of a proliferation of cells not subject to the usual limitations of growth. As used herein, "anti-neoplastic agent" is any compound, composition, admixture, co-mixture or blend which inhibits, eliminates, retards or reverses the neoplastic phenotype of a cell.

Chemotherapy, surgery, radiation therapy, therapy with biologic response modifiers, and immunotherapy are currently used in the treatment of cancer. Each mode of therapy has specific indications which are known to those of ordinary skill in the art, and one or all may be employed in an attempt to achieve total destruction of neoplastic cells. Chemotherapy utilizing one or more taccalonolides is provided by the present invention. Moreover, combination chemotherapy, chemotherapy utilizing taccalonolides in combination with other neoplastic agents, is also provided by the subject invention as combination therapy is frequently more effective than the use of single anti-neoplastic agents. Thus, a further aspect of the present invention provides compositions containing a therapeutically effective amount of at least one taccalonolide compound of the present invention, including nontoxic addition salts thereof, which serve to provide the above-recited therapeutic benefits. Such compositions can also be provided together with physiologically tolerable liquid, gel or solid carriers, diluents, adjuvants, excipients, and the like, Such carriers, diluents, adjuvants and excipients may be found in the *United States Pharmacopeia Vol. XXII and National Formulary Vol XVII,* U.S. Pharmacopeia Convention, Inc., Rockville, Md. (1989), the contents of which are incorporated herein by reference. Additional modes of treatment are provided in *AHFS Drug Information,* 1993 ed. by the American Hospital Formulary Service, pp. 522–660, the relevant contents of which are incorporated herein by reference.

Certain embodiments of the present invention further provide that the pharmaceutical composition used to treat neoplastic disease contains at least one taccalonolide compound and at least one additional anti-neoplastic agent. Anti-neoplastic compounds which may be utilized in combination with taccalonolides include those provided in *The Merck Index,* 11th ed. Merck &Co., Inc. (1989) pp. Ther 16–17, the contents of which are hereby incorporated by reference. In a further embodiment of the invention, anti-neoplastic agents may be antimetabolites which include methotrexate, 5-fluorouracil, 6-mercaptopurine, cytosine arabinoside, hydroxyurea, 2-chlorodeoxyadenosine, and the like.

In another embodiment of the present invention, the anti-neoplastic agents contemplated are alkylating agents which include cyclophosphamide, melphalan, busulfan, paraplatin, chlorambucil, nitrogen mustard, and the like. In a further embodiment of the subject invention, the anti-neoplastic agents are plant-derived natural products which include vincristine, vinblastine, taxol, etoposide, and the like. In a further embodiment of the present invention, the anti-neoplastic agents contemplated are antibiotics which include doxorubicin (adriamycin), daunorubicin, mitomycin c, bleomycin, and the like.

In a further embodiment of the subject invention, the anti-neoplastic agents contemplated are hormones which include calusterone, diomostavolone, propionate, epitiostanol, mepitiostane, testolactone, tamoxifen, polyestradiol phosphate, megesterol acetate, flutamide, nilutamide, trilotane, and the like. In a further embodiment of the subject invention, the anti-neoplastic agents contemplated include enzymes such as L-Asparaginase, aminoacridine derivatives, (e.g., amsacrine), and the like. Additional anti-neoplastic agents include those provided in Skeel, Roland T., "Antineoplastic Drugs and Biologic Response Modifier: Classification, Use and Toxicity of Clinically Useful Agents," *Handbook of Cancer Chemotherapy* (3rd ed.), Little Brown & Co. (1991), the relevant contents of which are incorporated herein by reference.

The present taccalonolide compounds and compositions can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 mg/kg, more usually 0.01 to 10 mg/kg, of the host body weight. Alternatively, dosages within these ranges can be administered by constant infusion over an extended period of time, usually exceeding 24 hours, until the desired therapeutic benefits have been obtained. Indeed, drug dosage, as well as route of administration, must be selected on the basis of relative effectiveness, relative toxicity, growth characteristics of tumor and effect of taccalonolides on cell cycle, drug pharmacokinetics, age, sex, physical condition of the patient, and prior treatment.

The taccalonolide compounds, with or without additional anti-neoplastic agents, may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups and will generally be formed with inorganic acids such as, for example, hydrochloric or phosphoric acids, or organic acids such as acetic, oxalic, tartaric, mandelic, and the like. Additional excipients which are contemplated for use in the practice of the present invention are those available to those of ordinary skill in the art, for example, those found in the *United States Pharmacopeia Vol, XXII and National Formulary Vol XVII*, U.S. Pharmacopeia Convention, Inc., Rockville, Md. (1989), the relevant contents of which is incorporated herein by reference.

The suitability of particular carriers for inclusion in a given therapeutic composition depends on the preferred route of administration. For example, anti-neoplastic compositions may be formulated for oral administration. Such compositions are typically prepared either as liquid solution or suspensions, or in solid forms. Oral formulations usually include such normally employed additives such as binders, fillers, carriers, preservatives, stabilizing agents, emulsifiers, buffers and excipients such as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

Compositions of the present invention may also be prepared as injectable, either as liquid solutions, suspensions, or emulsions; solid forms suitable for solution in, or suspension in, liquid prior to injection may be prepared. Such injectables may be administered subcutaneously, intravenously, intraperitoneally, intramuscularly, intrathecally, intrapleurally, and the like. The active ingredient or ingredients are often mixed with diluents or excipients which are physiologically tolerable and compatible with the active ingredient(s). Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

The invention further provides methods for using taccalonolide compounds encompassed by the generic structure set forth above to inhibit the proliferation of mammalian cells by contacting these cells with a taccalonolide compound in an amount sufficient to inhibit the proliferation of the mammalian cell. A preferred embodiment embraces inhibiting the proliferation of hyperproliferative mammalian cells. For purposes of this invention "hyperproliferative mammalian cells" are mammalian cells which are not subject to the characteristic limitations of growth, e.g., loss of growth control and insensitivity to normal programmed cell death (apoptosis). A further preferred embodiment is when the mammalian cell is human. The invention further provides for contacting the mammalian cell with at least one taccalonolide compound and at least one additional anti-neoplastic agent. The types of anti-neoplastic agents contemplated are the same as those disclosed hereinabove.

The invention further provides methods for using taccalonolide compounds encompassed by the generic structure set forth above to inhibit the proliferation of hyperproliferative cells with drug-resistant phenotypes, including those with multiple drug-resistant phenotypes, by contacting said cell with a taccalonolide compound in an amount sufficient to inhibit the proliferation of a hyperproliferative mammalian cell. A preferred embodiment is when the mammalian cell is human. The invention further provides contacting the mammalian cell with a taccalonolide compound and at least one additional anti-neoplastic agent. The types of anti-neoplastic agents contemplated the same as those disclosed hereinabove.

The invention further provides a method for alleviating pathological conditions caused by hyperproliferating mammalian cells, for example, neoplasia, by administering to a subject in need thereof an effective amount of a taccalonolide as described herein to inhibit the proliferation of the hyperproliferating cells. As used herein "pathological condition" refers to any pathology arising from the proliferation of mammalian cells that are not subject to the normal limitations of cell growth. Such proliferation of cells may be due to neoplasms, including mammary, small-cell lung, non-small-cell lung, colorectal, leukemia, melanoma, central nervous system (CNS), ovarian, prostate, sarcoma of soft tissue or bone, head and neck, gastric (which includes pancreatic and esophageal), stomach, myeloma, bladder, renal, neuroendocrine (which includes thyroid), lymphoma, non-Hodgkin's, Hodgkin's disease neoplasms, and the like. In a further embodiment of the invention, the neoplastic cells are human. The present invention further provides methods of alleviating such pathological conditions utilizing taccalonolide in combination with other therapies, as well as other anti-neoplastic agents. Such therapies and their appropriateness for different neoplasia may be found in *Cancer Principles and Practice of Oncology*, 4$^{th}$ ed., Editors DeVita, V., Hellman, S., and Rosenberg, S., Lippincott Co. (1993), the contents of which are incorporated herein by reference.

In the present disclosure, taccalonolide compounds are shown to potently stabilize the microtubule structure in cultured cells. In addition, and in contrast with the Vinca alkaloids and taxol, taccalonolide compounds appear to be a poor substrate for the drug-efflux pump P-glycoprotein.

The following examples serve to illustrate certain embodiments and aspects of the present invention and are not to be construed as limiting the scope thereof.

Reagents 4,6-Diamidino-2-phenylindole (DAPI), sulforhodamine B (SRB), antibodies against β-tubulin, and Basal Medium Eagle containing Earle's salts (BME) were obtained from the Sigma Chemical Company (St. Louis, Mo.). Richter's medium was obtained from BioWhittaker (Walkersville, Md.) and Fetal Bovine Serum (FBS) was obtained from Hyclone Laboratories (Logan, Utah).

EXAMPLE 1

Isolation and Purification of Taccalonolide A

Taccalonolide A was obtained as a lipophilic extract of *Tacca chantrieri* obtained from the Lyon Arboretum (Honolulu, Hi.), and subjected to bioassay-directed purification. Lyophilized tubers of *Tacca chantrieri* were ground to a fine powder and extracted twice by stirring with dichloromethane/isopropanol (7/3 v/v) for 24 hours at room temperature. The extraction was repeated under identical conditions with fresh solvent, solids were filtered off, and the combined extracts were evaporated in vacuo below 40° C.

The residue was dissolved in 90% (v/v) aqueous methanol and extracted three times with equal volumes of hexanes, and the hexane fractions were discarded. The aqueous methanol phase was diluted with water to 80% (v/v) aqueous methanol and extracted three times with equal volumes of toluene. The combined toluene fractions were evaporated in vacuo below 40° C. to dryness. The residue was dissolved in a minimum amount of dichloromethane and applied to a silica gel column equilibrated in ether, and the column was eluted with ether Active fractions were combined and rechromatographed over silica gel using a solvent system of 75% methyl-tert-butyl ether/25% hexanes (v/v) containing 1% isopropanol.

EXAMPLE 2

Cell Culture

A-10 rat aortic smooth muscle cells, SK-OV-3 human ovarian carcinoma cell line and HeLa cells were obtained from the American Type Culture Collection (Manassas, Va.) and were cultured in BME containing 10% FBS and 50 μg/1 mL gentamycin sulfate. A sub-line of SK-OV-3 selected for resistance to vinblastine (SKVLB-1) was provided by Dr. Victor Ling (British Columbia Cancer Center, Vancouver, British Columbia) and was maintained in BME containing 10% FBS and 50 μg/1 mL gentamycin sulfate. The A-10, HeLa, SK-OV-3, and SKVBL-1 cells were grown in Basal Medium Eagle containing Earle's salts, 50 μg/ml gentamycin, and 10% fetal bovine sorum (Hyclone, Logan Utah). Vinblastine was added to a final concentration of 1 μg/mL to SKVLB-1 cells 24 hours after passage to maintain selection pressure for P-glycoprotein-overexpressing cells. The MDA-MB-435 human mammary adenocarcinoma cell line was obtained Dr. Mai Higazi (Georgetown University, Washington, D.C.), and was maintained in Richters medium containing 10% FBS and 50 μg/mL gentamycin sulfate.

EXAMPLE 3

Inhibition of Cell Proliferation

The IC$_{50}$ for inhibition of cell proliferation was determined by measuring cell-associated protein after drug treatment using the sulforhodamine B assay (see, for example, J. Natl. Cancer Inst. 82:1107–1112 (1990) and Drug Development Res. 34:91–109 (1995)).

EXAMPLE 4

Immunofluorescence Assays

A-10 cells were grown to 70–85% confluency on glass coverslips in BME/10% FBS. Drug compounds in PBS were added to the indicated final concentrations and cells were incubated for an additional 24 hours. For the staining of microtubules and intermediate filaments, the cells were fixed with cold methanol for 5 minutes, blocked for 20 minutes with PBS containing 10% calf serum to block nonspecific binding sites, and incubated at 37° C. for 60–90 min with monoclonal anti-β-tubulin at the dilutions recommended by the manufacturer. Bound primary antibodies were subsequently visualized by a one hour incubation with fluorescein (FITC)-conjugated sheep antimouse IgG (F-3008; Sigma). The coverslips were washed, stained with 0.1 μg/mL DAPI for 10 minutes, mounted on microscope slides and the fluorescence patterns were examined and photographed using a Zeiss Axioplan microscope equipped with epifluorescence optics for fluorescein and DAPI.

EXAMPLE 5

Cell Cycle Analysis

MDA-MB-435 cells were treated with the IC$_{85}$ concentration of taccalonolide, 10 μM, or vehicle control for 6, 12, 18 or 24 hr. The cells were fixed in 70% ethanol, treated with RNAse A and stained with propidium iodide as described by Mooberry et al., in Int. J. Cancer 73:440–448 (1997). The DNA content was analyzed using a Coulter EPICS XL-MCL flow cytometer and the data were plotted as number of events vs. propidium iodide fluorescence intensity. See FIGS. 3A–3D.

EXAMPLE 6

Caspase 3 Activity

Caspase-3 activity was measured by cleavage of DEVD-pNA using the BIOMOL Caspase-3 Cellular Activity Kit Plus (AK-703). MDA 435 cells were incubated with 10 μM taccalonolide, the $IC_{85}$ concentration, for up to 24 hr. Following the incubation the cells were harvested, washed, and lysed and the cell lysates immediately frozen at −70° C. The protein concentration of the lysates was determined (Pierce Reagent, Rockford Ill.) and samples containing 30 μg protein were incubated in duplicate with the substrate DEVD-pNA at 37° C. Controls consisted of samples containing the caspase inhibitor Ac-DEVD-CHO, caspase-3 positive controls, with and without Ac-DEVD-CHO and reagent blanks. Enzymatic cleavage of DEVD-pNA was measured spectrophotometrically as an increase in absorbance at 405 nm in a microtiter plate reader.

EXAMPLE 7

Immunoblot Analysis

MDA-MB-435 cells were treated with taccalonolide at the IC85 concentration for inhibition of proliferation for 0–24 h. Following drug exposure the cells were harvested and cellular proteins extracted in radioimmunoprecipitation buffer in the presence of protease inhibitors as described previously (see Mooberry et al., Supra). The protein concentrations of the samples were determined (Pierce Reagent, Rockford, Ill.) and cell lysate aliquots containing equal concentrations of protein were separated, transferred, probed with specific antibodies, and detected as previously described (see Mooberry et al., in Cancer Res. 59:653–660 (1999)). The Bcl-2 and caspase 3 antibodies were purchased from PharMingin (San Diego, Calif.).

EXAMPLE 8

Tubulin and Microtubule Protein Assembly

The assembly of purified tubulin was monitored spectrophotometrically by the change in absorbance at 340 nm. Purified glycerol-free bovine brain tubulin (TL-238, Cytoskeleton, Denver, Colo.) was solubilized in ice cold G-PEM buffer (80 mM PIPES, pH 6.9, 1 mM $MgCl_2$, 1 mM EGTA and 1 mM GTP) and taccalonolide, Taxol or vehicle control was added and mixed well. The final concentration of tubulin was 1 mg/ml and ethanol concentration was 1% or less. An aliquot of the mixture was transferred to a room temperature 96 well plate and tubulin polymerization monitored for 60 min. at 35° C. in a temperature controlled microplate spectrophotometer.

The assembly of MAP-rich microtubule protein was examined using the CytoDYNAMIX Screen 01 (Cytoskeleton, Denver Colo.). MAP-rich tubulin (ML113) was reconstituted to 1 mg/ml with 80 mM G-PEM buffer containing vehicle control (0.2% ethanol), taccalonolide (200 μM), or Taxol (2 μM). The assay used a 96 well format in a temperature controlled microplate reader. Microtubule protein polymerization was measured by change of absorbance at 340 nm at 37° C. for 60 min.

EXAMPLE 9

Electron Microscopy

Samples of the tubulin polymers formed in the presence of taccalonolide, Taxol, vehicle or buffer alone during the tubulin polymerization experiments described above were applied to 300 mesh carbon-coated Formvar-treated copper grids, strained with 1% uranyl acetate and examined using a LEO 912 energy filter transmission electron microscope.

EXAMPLE 10

Effects of Taccalonolide and Paclitaxel on Cellular Microtubules

Strong paclitaxel-like microtubule-stabilizing activity was found in the crude lipophilic extract from the plant *T. chantrieri*. Bioassay directed purification of the extract yielded the microtubule active-compound taccalonolide A. Studies with the purified compound show that taccalonolide A caused dramatic reorganization of cellular microtubules in interphase and mitotic cells.

A-10 cells were treated with taccalonolide A, or paclitaxel for 18–24 hours and the drug's effects on microtubules examined by indirect immunofluorescence. The control cells exhibited normal microtubules arrays. Treatment of the cells with taccalonolide A disrupted the normal microtubule array with the microtubules radiating from the central regions of the cell, the microtubule organizing center, to the cell periphery. Although the microtubule network is extensive it does not occupy the entire cytosol. Taccalonolide, at concentrations of 0.1–0.5 μM, caused a slight increase in the density of cellular microtubules, but at concentrations of 5 μM–50 μM, significant alterations of the normal microtubules network occurred. A 10 μM concentration of taccalonolide caused at least two effects in the A-10 cells. Some cells had a much higher density of long thick microtubules that filled more of the cytoplasm, similar to the effects of paclitaxel, while other adjacent cells showed the appearance of short thick tufts of microtubules that appear to nucleate independent of the microtubule organizing center. More of the cells exhibited the formation of the short thick microtubules and at concentrations higher than 10 μM all cells contained thick short tufts of microtubules that were more prevalent in the cell periphery.

Paclitaxel at concentrations between 1–20 μM initiated the formation of a highly organized array of microtubules, some of which formed thick microtubule bundles. Long microtubule bundles often surrounded the nucleus. The extensive long hoops and bundles that formed after treatment with 2 μM paclitaxel were not seen with taccalonolide.

An interesting difference between the taccalonolide-treated cells and the paclitaxel-treated cells occurred with respect to cell shape. The taccalonolide treated cells tended to retain a rounder shape like untreated or vehicle-treated controls while the paclitaxel-treated cells were more elongated than either control or taccalonolide treated cells. Microtubules in cells treated with taccalonolide were resistant to the microtubule depolymerizing effects of vinblastine, consistent with the effects of paclitaxel.

EXAMPLE 11

Effects of Taccalonolide on Mitotic Spindles and Mitotic Progression

A common characteristic of antimicrotubule agents is their ability to disrupt normal mitosis due to inhibition of the highly dynamic mitotic spindles. The effects of taccalonolide on mitotic spindles were examined in A-10 and HeLa cells. In both cell lines taccalonolide caused the appearance of abnormal multi-polar mitotic spindles. Normal mitotic spindles are bipolar. The mitotic spindles formed in taccalonolide-treated cells contained 3 or more spindle poles that did not show coordinated orientation These abnormal mitotic spindles were unable to align the DNA in metaphase. A dose-response study showed that the first observable cellular changes with a low concentration of taccalonolide (0.5 μM) was abnormal coordination of the DNA in the metaphase plate during mitosis, even in the presence of only two mitotic spindles.

Abnormal mitotic spindles arrest the cells in the G2/M phase of the cell cycle and thus the effects of taccalonolide on cell cycle progression were examined by flow cytometry.

Normal cell cycle distribution was seen in the vehicle treated MDA-MB-435 cells (FIG. 3A) and mitotic blockade was evident within 6 hr of taccalonolide treatment (FIG. 3B) and the blockade progressed to complete G2/M arrest at 12 and 24 hrs (FIGS. 3C, 3D). There was no evidence of release from mitotic blockade and with the 24 hr time points the appearance of the subG1 peak suggests that the cells are undergoing apoptotic cell death (see Darzynkiewicz et al., in Cytometry 13:795–808 (1992)).

EXAMPLE 12

Taccalonolide Initiates the Formation of Micronuclei

Cells treated with taccalonolide exhibited abnormal nuclear organization and the breakdown of the nucleus into multiple micronuclei. These effects are also seen in Taxol-treated cells and taccalonolide and Taxol were equipotent at initiating the formation of the micronuclei in A-10 cells. In A-10 cells these nuclear changes occur in cells containing interphase microtubules. The nuclear reorganization in this cell line is not dependent on mitotic arrest. Micronuclei were also exhibited in taccalonolide treated HeLa cells.

EXAMPLE 13

Effects of Taccalonolide and Paclitaxel on Cell Proliferation of Drug-Sensitive and Multidrug-Resistant Cell Lines The $IC_{50}$ values for taccalonolide were determined in two drug-sensitive cell lines, MDA-MBA-435 and SK-OV3, and in a multidrug-resistant cell line, SKVLB-1 See Table 1. Cells were treated with a range of concentrations of taccalonolide for 48 hr and the inhibition of proliferation determined using the SRB assay. The $IC_{50}$ for each cell line was calculated from the dose response curves. The resistance factor was calculated by dividing the $IC_{50}$ of the drug sensitive cell line by the $IC_{50}$ of the drug resistant cell line. The values represent the mean of 3 or 4 experiments ± the SD.

TABLE 1

| Cell Line | $IC_{50}$ ($\mu$M) Taccalonolide A $\mu$M |
|---|---|
| MDA-MB-435 | 2.1 ± 0.3 |
| SK-OV-3 | 2.3 ± 0.9 |
| SKVLB-1 | 656 ± 42 |
| Resistance factor | 285 |

Taccalonolide A is found to be a potent inhibitor of cell proliferation with $IC_{50}$ values in the low $\mu$M range. In contrast to paclitaxel, Taccalonolide A is able to completely inhibit the proliferation of the SKVLB-1 cell line that overexpresses the drug efflux pump P-glycoprotein. The resistance factor (which is calculated by dividing the $IC_{50}$ of the sensitive cell line by the $IC_{50}$ in the resistant cell line) between the parental, drug-sensitive line (SK-OV-3) and the drug resistant cell line (SKVLB-1) is 285, the resistance factor for paclitaxel with these cell lines is greater than 58,000 (see Mooberry et al., in Cancer Res. 59:653–660 (1999)). The resistance factors for other microtubule agents in these two cells lines is 105 for laulimalide and 1.1 for cryptophycin 1 (see Mooberry et al., Supra, and Smith et al., in Cancer Res. 54:3779–3784 (1994)). Taccalonolide appears to be a poor substrate for p-glyprotein mediated drug transport. Paclitaxel did not achieve >70% inhibition of the SKVLB-1 cell line with concentrations of up to 100 $\mu$M. Thus, taccalonolide A was significantly more effective against the SKVLB-1 cell line than paclitaxel. These data confirm that these taccalonolide agents are poor substrates for transport by P-glycoprotein.

EXAMPLE 14

Taccalonolide Initiates Bcl-2 Phosphorylation and Apoptosis

Taccalonolide initiated the breakdown of the nucleus into micronuclei, a characteristic of apoptosis and a sub G1 peak was measured by flow cytometry in taccalonolide-treated cells. A common feature of apoptosis induced by agents that target microtubules is the phosphorylation of Bcl-2, a cellular regulator of apoptosis. The effects of taccalonolide on Bcl-2 were investigated by immunoblotting techniques. The appearance of a slower migrating form of Bcl-2 is consistent with Bcl-2 phosphorylation. The slower migrating form of Bcl-2 is apparent within about 18 hours of treatment, and persists at 24 hours (see FIG. 4). The apoptotic pathway induced by taccalonolide A, like paclitaxel, involves Bcl-2 phosphorylation.

One characteristic of apoptosis is the activation of the caspase cascade of proteinases that are responsible for the initiation and execution phases of apoptosis. Caspase 3 activation is a hallmark of late events in apoptosis. Caspsase 3 activity of cell lysates prepared from cells treated with 10 $\mu$M taccalonolide (the $IC_{85}$) showed activation of the caspase over the time course of 8–24 hr (see FIG. 5). Immunoblotting techniques with caspase 3 antibody confirmed the activation of the caspase by the appearance of the p17 subunit of the activated caspase. The p17 product was detected 18 and 24 hrs following taccalonolide treatment. The data suggest that taccalonolide initiates apoptotic cell death in the MDA-MB-435 cell line.

EXAMPLE 15

Effects of Taccalonolide on Tubulin and Microtubule Protein Polymerization

Microtubule stabilizing agents are able to stimulate the polymerization of purified tubulin under conditions where very little tubulin polymerization occurs. The effect of taccalonolide on tubulin polymerization was measured spectrophotometrically by the absorbance at 350 nm. Increased turbidity of the solution, constant with tubulin polymerization is measured over time. Taccalonolide stimulated the polymerization of tubulin, consistent with its effects in cells but it was much less potent than Taxol (FIG. 6). Electron microscopy revealed that the polymers formed in the presence of taccalonolide resembled tubules and at high magnification were indistinguishable from Taxol-initiated polymers.

Figure 1:
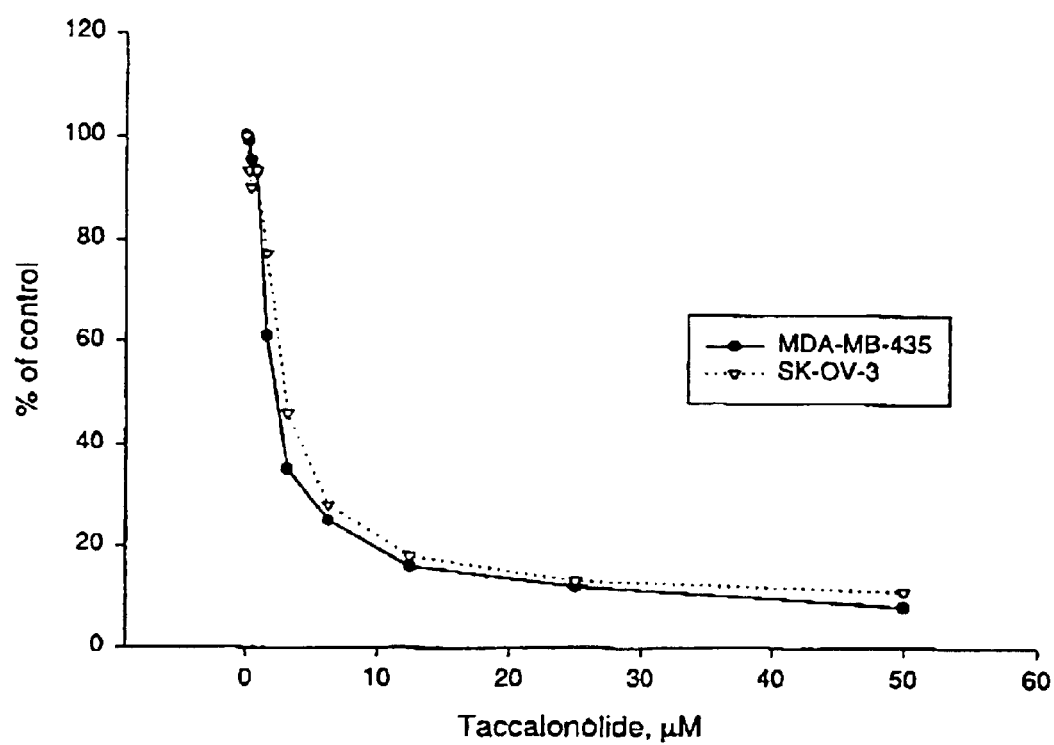
FIG. 1 illustrates the effect of taccalonolide A on two different cancer cell lines as a function of concentration. Darkened circles represent results with MDA-MB-435 human mammary adenocarcinoma cell line and the open triangles represent results with SK-OV-3 human ovarian carcinoma cell line.
Figure 2:
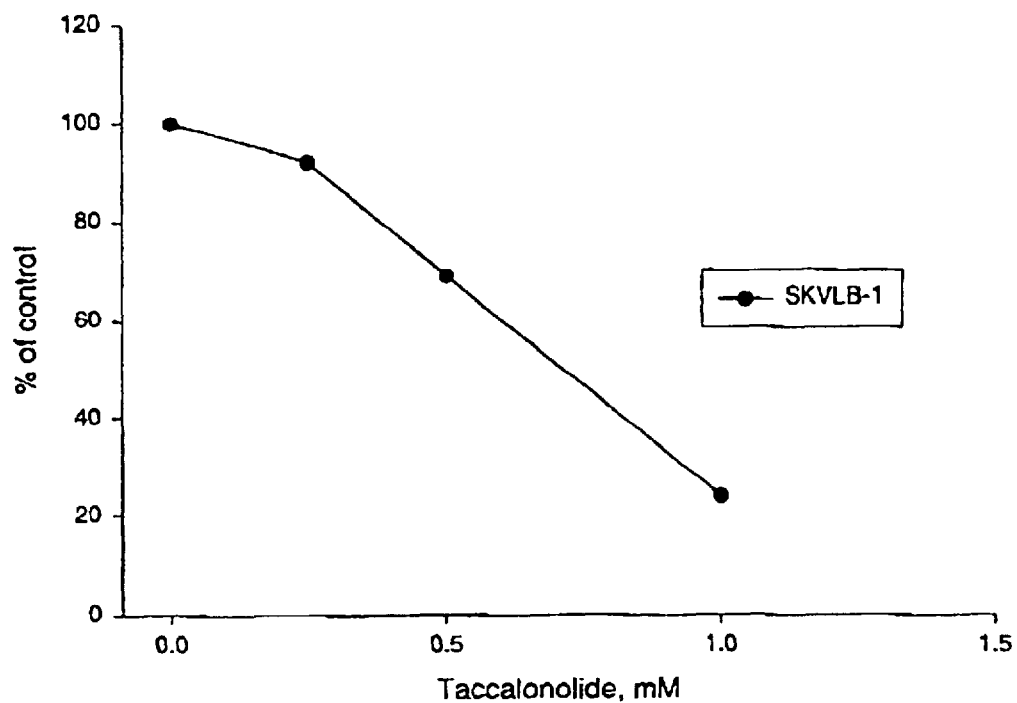
FIG. 2 illustrates the effect of taccalonolide A on the drug resistant cell line SKVLB-1 (a sub-line of SK-OV-3 selected for resistance to vinblastine).

Taccalonolide A has been shown to inhibit the proliferation of drug sensitive and drug resistant cancer cell lines. (See FIGS. 1 and 2).

Taccalonolide agents have been shown to be paclitaxel-like stabilizers of microtubules that cause alterations of both interphase and mitotic microtubules. For example, Taccalonolide A is a potent inhibitor of cell proliferation and initiates micronuclei formation. Taccalonolide A is superior to paclitaxel in the ability to circumvent P-glycoprotein-mediated drug resistance. The taccalonolides therefore represent a new class of paclitaxel-like microtubule-stabilizing agents with properties that may provide advantages over the taxanes.

The clinical success of the taxanes in treating a wide range of tumors has lead to the search for new agents with a similar mechanism of action. It has now been demonstrated that taccalonolide compounds of the present invention are potent inhibitors of cell proliferation, acting by disruption of the microtubule network. The taccalonolide compounds disrupt microtubule organization and thus normal cellular functions, including those of mitosis.

The present invention demonstrates that taccalonolide compounds circumvent P-glycoprotein-mediated multiple drug resistance. Transport by P-glycoprotein limits the ability of natural product anticancer drugs to inhibit the growth of tumor cells with acquired or de nova drug resistance. Paclitaxel, while very useful in the initial course of chemotherapy, is a substrate for transport by P-glycoprotein, and so is of limited usefulness against P-glycoprotein-mediated MDR tumors. Therefore, identification of agents which overcome multiple drug resistance should lead to the development of useful and novel anticancer agents. The taccalonolide compounds of the present invention appear to be such agents since they are poor substrates for P-glycoprotein mediated transport. This fact is reflected in the low cell resistance factor for taccalonolide agents compared with paclitaxel and numerous other natural product drugs.

While the invention has been described in detail with reference to certain preferred embodiments thereof, it will be understood that modifications and variations are within the spirit and scope of that which is described and claimed.

What is claimed is:

1. A method of inhibiting the proliferation of a hyperproliferative mammalian cell having a multiple drug resistant phenotype, said method comprising contacting a hyperproliferative mammalian cell having a multiple drug resistant phenotype with an amount of a taccalonolide compound effective to disrupt the dynamic state of microtubule polymerization and depolymerization to arrest cell mitosis, thereby inhibiting the proliferation of the cell, wherein said taccalonolide has the structure:

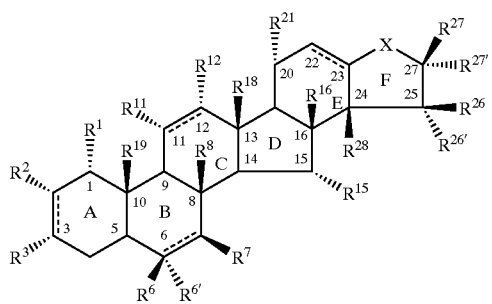

wherein:
$R^1$=hydroxy, lower alkoxy or acyloxy,
$R^2$=OH, or $R^2$ and $R^3$ cooperate to form an epoxide at C-2/C-3,
$R^3$=OH, or $R^3$ cooperates with $R^2$ to form an epoxide at C-2/C-3,
$R^6$=OH, or a carbonyl oxygen if $R^{6'}$ is not present,
$R^{6'}$, when present, is H,
$R^7$=hydroxy, lower alkoxy or acyloxy,
$R^8$=H,
$R^{11}$=H, hydroxy, lower alkoxy or acyloxy,
$R^{12}$=hydroxy, lower alkoxy or acyloxy,
$R^{15}$=hydroxy, tower alkoxy or acyloxy,
$R^{16}$=H,
$R^{18}$=H or lower alkyl,
$R^{19}$=lower alkyl,
$R^{21}$=lower alkyl,
$R^{26}$=hydroxy, lower alkoxy or acyloxy,
$R^{26'}$=lower alkyl,
$R^{27}$=carbonyl oxygen and $R^{27'}$ is not present,
$R^{28}$=H or lower alkyl; and
X=O, and
wherein the dashed lines between C2/C3, C6/C7, C11/C2 and C22/23 represent optional double bonds at each position.

2. A method according to claim 1 wherein:
$R^1$ is —O-acetyl,
$R^2$ and $R^3$ cooperate to form an epoxide,
$R^6$ is a carbonyl oxygen and $R^{6'}$ W is not present,
$R^7$ is hydroxy,
$R^8$ is H,
$R^{11}$ is —O-acetyl,
$R^{12}$ is —O-acetyl,
$R^{15}$ is —O-acetyl,
$R^{16}$ is H,
$R^{18}$ is methyl,
$R^{19}$ is methyl,
$R^{21}$ is methyl,
$R^{26}$ is hydroxy,
$R^{26'}$ is methyl,
$R^{27}$ is a carbonyl oxygen and $R^{27'}$ is not present,
$R^{28}$ is methyl,
X is O, and
there is a double bond between C22 and C23 (taccalonolide A).

3. A method according to claim 1 wherein:
$R^1$ is O-acetyl,
$R^2$ and $R^3$ cooperate to form an epoxide,
$R^6$ is a carbonyl oxygen and $R^{6'}$ is not present,
$R^7$ is hydroxy,
$R^8$ is H,
$R^{11}$ is O-acetyl,
$R^{12}$ is O-acetyl,
$R^{15}$ is hydroxy,
$R^{16}$ is H,
$R^{18}$ is methyl,
$R^{19}$ is methyl
$R^{21}$ is methyl,
$R^{26}$ is hydroxy,
$R^{26'}$ is methyl,
$R^{27}$ is a carbonyl oxygen and $R^{27'}$ is not present,
$R^{28}$ is methyl,
X is O, and
there is a double bond between C22 and C23 (taccalonolide B).

4. A method according to claim 1 wherein:

$R^1$ is O-acetyl, $R^2$ and $R^3$ cooperate to form an epoxide, $R^6$ is a carbonyl oxygen and $R^{6'}$ is not present, $R^7$ is O-acetyl, $R^8$ is H, $R^{11}$ is O-acetyl, $R^{12}$ is O-acetyl, $R^{15}$ is hydroxy, $R^{16}$ is H, $R^{18}$ is methyl, $R^{19}$ is methyl, $R^{21}$ is methyl, $R^{26}$ is hydroxy, $R^{26'}$ is methyl, $R^{27}$ is a carbonyl oxygen and $R^{27'}$ is not present, $R^{28}$ is methyl, X is O, and there is a double bond between C22 and C23 (taccalonolide D).

5. A method according to claim 1 wherein:

$R^1$ is O-acetyl, $R^2$ and $R^3$ cooperate to form an epoxide, $R^6$ is a carbonyl oxygen and $R^{6'}$ is not present, $R^7$ is hydroxy or O-acetyl, $R^8$ is H, $R^{11}$ is O-acetyl, $R^{12}$ is O-acetyl, $R^{15}$ is hydroxy or O-acetyl, $R^{16}$ is H, $R^{18}$ is H or methyl, $R^{19}$ is methyl, $R^{21}$ is methyl, $R^{26}$ is hydroxy, $R^{26'}$ is methyl, $R^{27}$ is a carbonyl oxygen and $R^{27'}$ is not present, $R^{28}$ is H or methyl, X is O, and there is a double bond between C22 and C23.

6. A method according to claim 1 further comprising administering an anti-neoplastic agent in conjunction with said taccalonolide.

7. A method of alleviating a pathological condition caused by hyperproliferating, multiple drug resistant mammalian cells, said method comprising administering an amount of a taccalonolide compound to a subject having a hyperproliferative pathological condition and a multiple drug resistant phenotype effective to disrupt the dynamic state of microtubule polymerization and depolymerization to arrest cell mitosis, thereby alleviating said pathological condition, wherein said taccalonolide has the structure:

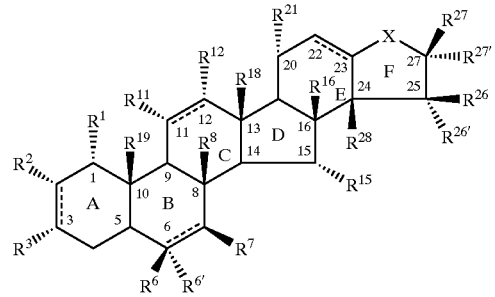

wherein;

$R^1$=hydroxy, lower alkoxy or acyloxy, $R^2$=OH, or $R^2$ and $R^3$ cooperate to form an epoxide at C-2/C-3, $R^3$=OH, or $R^3$ cooperates with $R^2$ to form an epoxide at C-2/C-3, $R^6$=OH, or a carbonyl oxygen if $R^{6'}$ is not present, $R^{6'}$, when present, is H, $R^7$=hydroxy, lower alkoxy Or acyloxy, $R^8$=H, $R^{11}$=H, hydroxy, lower alkoxy or acyloxy, $R^{12}$=hydroxy, lower alkoxy or acyloxy, $R^{15}$=hydroxy, lower alkoxy or acyloxy, $R^{16}$=H, $R^{18}$=H or lower alkyl, $R^{19}$=lower alkyl, $R^{21}$=lower alkyl, $R^{26}$=hydroxy, lower alkoxy or acyloxy, $R^{26'}$=lower alkyl, $R^{27}$=a carbonyl oxygen and $R^{27'}$ is not present, $R^{28}$=H or lower alkyl; and X=O, and wherein the dashed lines between C2/C3, C6/C7, C11/C12 and C22/23 represent optional double bonds at each position.

8. A method according to claim 7, further comprising administering to said subject at least one additional therapeutic for said pathological condition.

9. A method according to claim 7, wherein said pathological condition is characterized by the formation of neoplasms.

10. A method according to claim 9, wherein said neoplasm is selected from the group consisting of mammary, small-cell lung, non-small-cell lung, colorectal, leukemia, melanoma, pancreatic adenocarcinoma, central nervous system (CNS), ovarian, prostate, sarcoma of soft tissue or bone, head and neck, gastric which includes pancreatic and esophageal, stomach, myeloma, bladder, renal, neuroendocrine which includes thyroid and non-Hodgkin's disease and Hodgkin's disease neoplasms.

11. A method to inhibit the proliferation of mammalian cells with drug-resistant phenotype, said method comprising contacting said mammalian cells with drug resistant phenotype with a taccalonolide compound in an amount sufficient to inhibit the proliferation of the mammalian cells, wherein said taccalonolide has the structure:

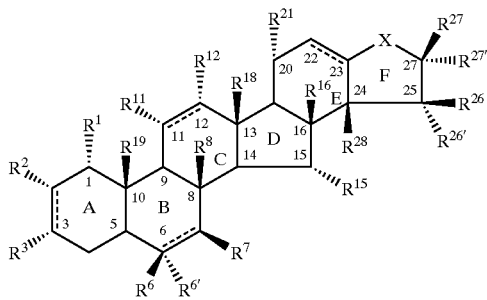

wherein:
R$^1$=hydroxy, lower alkoxy or acyloxy,
R$^2$=OH, or R$^2$ and R$^3$ cooperate to form an epoxide at C-2/C-3,
R$^3$=OH, or R$^3$ cooperates with R$^2$ to form an epoxide at C-2/C3,
R$^6$=OH, or a carbonyl oxygen if R$^{6'}$ is not present,
R$^{6'}$, when present, is H,
R$^7$=hydroxy, lower alkoxy or acyloxy,
R$^8$=H,
R$^{11}$=H, hydroxy, lower alkoxy or acyloxy,
R$^{12}$=hydroxy, lower alkoxy or acyloxy,
R$^{15}$=hydroxy, lower alkoxy or acyloxy,
R$^{16}$=H,
R$^{18}$=H or lower alkyl,
R$^{19}$=lower alkyl,
R$^{21}$=lower alkyl,
R$^{26}$=hydroxy, lower alkoxy or acyloxy,
R$^{26'}$=lower alkyl,
R$^{27}$=carbonyl oxygen and R$^{27'}$ is not present,
R$^{28}$=H or lower alkyl; and
X=O, and
wherein the dashed lines between C2/C3, C6/C7, C11/C12 and C22/23 represent optional double bonds at each position.

12. A method to inhibit the proliferation of hyperproliferative cells with drug-resistant phenotype, said method comprising contacting hyperproliferative cells with drug resistant phenotype with a taccalonolide compound in an amount sufficient to inhibit the proliferation of said hyperproliferative cells, wherein said taccalonolide has the structure:

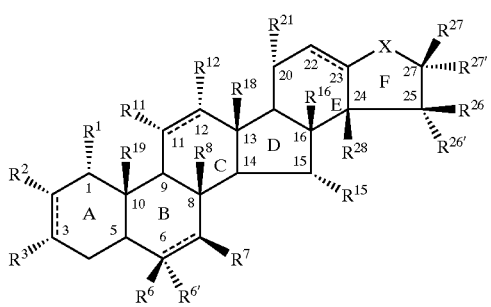

wherein;
R$^1$=hydroxy, lower alkoxy or acyloxy,
R$^2$=OH, or R$^2$ and R$^3$ cooperate to form an epoxide at C-2/C-3,
R$^3$=OH, or R$^3$ cooperates with R$^2$ to form an epoxide at C-2/C-3,
R$^6$=OH, or a carbonyl oxygen if R$^{6'}$ is not present,
R$^{6'}$, when present, is H,
R$^7$=hydroxy, lower alkoxy or acyloxy,
R$^8$=H,
R$^{11}$=hydroxy, lower alkoxy or acyloxy,
R$^{12}$=hydroxy, lower alkoxy or acyloxy,
R$^{15}$=hydroxy, lower alkoxy or acyloxy,
R$^{16}$=H,
R$^{18}$=H or lower alkyl,
R$^{19}$=lower alkyl,
R$^{21}$=lower alkyl,
R$^{26}$=hydroxy, lower alkoxy or acyloxy,
R$^{26'}$=lower alkyl,
R$^{27}$=carbonyl oxygen and R$^{27'}$ is not present,
R$^{28}$=H or lower alkyl; and
X=O, and
wherein the dashed lines between C2/C3, C6/C7, C11/C12 and C22/23 represent optional double bonds at each position.

13. A method for alleviating a pathological condition caused by mammalian cells with drug-resistant phenotype, said method comprising contacting mammalian cells with drug resistant phenotype with a taccalonolide compound in an amount sufficient to alleviate said pathological condition, wherein sold taccalonolide has the structure;

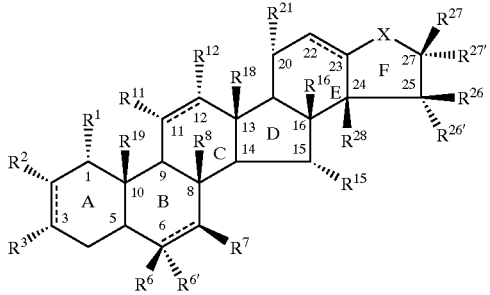

wherein;
R$^1$=hydroxy, lower alkoxy or acyloxy,
R$^2$=OH, or R$^2$ and R$^3$ cooperate to form an epoxide at C-2/C-3,
R$^3$=OH, or R$^3$ cooperates with R$^2$ to form an epoxide at C-2/C-3,
R$^6$=OH, or a carbonyl oxygen if R$^{6'}$ is not present,
R$^{6'}$, when present, is H,
R$^7$=hydroxy, lower alkoxy or acyloxy,
R$^8$=H,
R$^{11}$=H, hydroxy, lower alkoxy or acyloxy,
R$^{12}$=hydroxy, lower alkoxy or acyloxy,
R$^{15}$=hydroxy, lower alkoxy or acyloxy,
R$^{16}$=H,
R$^{18}$=H or lower alkyl,
R$^{19}$=lower alkyl,
R$^{21}$=lower alkyl,
R$^{26}$=hydroxy, lower alkoxy or acyloxy,
R$^{26'}$=lower alkyl,
R$^{27}$=a carbonyl oxygen and R$^{27'}$ is not present, $R^{28}$=H or lower alkyl; and X=O, and wherein the dashed lines between C2/C3, C6/C7, C11/C12 and C22/23 represent optional double bonds at each position.

14. A method of alleviating a pathological condition caused by hyperproliferating, multiple drug resistant mammalian cells, said method comprising administering an amount of a taccalonolide compound to a subject having a hyperproliferative pathological condition and a multiple drug resistant phenotype effective to disrupt the dynamic state of microtubule polymerization and depolymerization to arrest cell mitosis, thereby alleviating said pathological condition, wherein said taccalonolide has the structure:

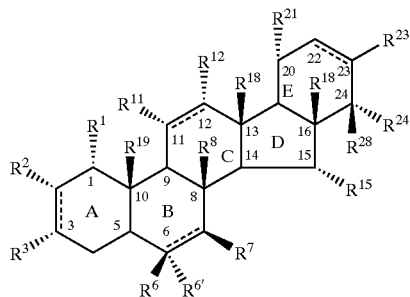

wherein:

$R^1$=hydroxy, lower alkoxy or acyloxy, $R^2$=OH, or $R^2$ and $R^3$ cooperate to form an epoxide at C-2/C-3, $R^3$=OH, or $R^3$ cooperates with $R^2$ to form an epoxide at C-2/C-3, $R^6$=OH, or a carbonyl oxygen it $R^{6'}$ is not present, $R^{6'}$, when present, is H, $R^7$=hydroxy, lower alkoxy or acyloxy, $R^8$=H, $R^{11}$=H, hydroxy, lower alkoxy or acyloxy, $R^{12}$=hydroxy, lower alkoxy or acyloxy, $R^{15}$=hydroxy, lower alkoxy or acyloxy, $R^{16}$=H, $R^{18}$=H or lower alkyl, $R^{19}$=lower alkyl, $R^{21}$=lower alkyl, $R^{23}$=hydroxy, lower alkoxy or acyloxy, $R^{24}$=hydroxy, lower alkoxy or acyloxy, and $R^{28}$=lower alkyl;

wherein the dashed lines between C2/C3, C6/C7, C11/C12 and C22/23 represent optional double bonds at each position.

15. A method to inhibit the proliferation of mammalian cells with drug-resistant phenotype, said method comprising contacting said mammalian cells with drug resistant phenotype with a taccalonolide compound in an amount sufficient to inhibit the proliferation of the mammalian cells, wherein said taccalonolide has the structure:

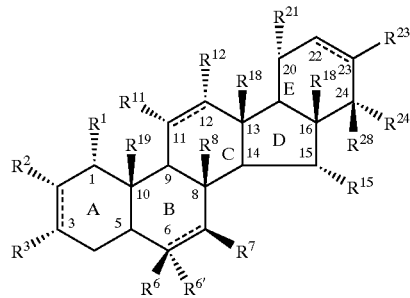

wherein:

$R^1$=hydroxy, lower alkoxy or acyloxy, $R^2$=OH, or $R^2$ and $R^3$ cooperate to form an epoxide at C-2/C-3, $R^3$=OH, or $R^3$ cooperates with $R^2$ to form an epoxide at C-2/C-3, $R^6$=OH, or a carbonyl oxygen if $R^{6'}$ is not present, $R^{6'}$, when present, is H, $R^7$=hydroxy, lower alkoxy or acyloxy, $R^8$=H, $R^{11}$=H, hydroxy, lower alkoxy or acyloxy, $R^{12}$=hydroxy, lower alkoxy or acyloxy, $R^{15}$=hydroxy, lower alkoxy or acyloxy, $R^{16}$=H, $R^{18}$=H or lower alkyl, $R^{19}$=lower alkyl, $R^{21}$=lower alkyl, $R^{23}$=hydroxy, lower alkoxy or acyloxy, $R^{24}$=hydroxy, lower alkoxy or acyloxy, and $R^{28}$=lower alkyl;

wherein the dashed lines between C2/C3, C6/C7, C11/C12 and C22/23 represent optional double bonds at each position.

16. A method to inhibit the proliferation of hyperproliferative cells with drug-resistant phenotype, said method comprising contacting hyperproliferative cells with drug resistant phenotype with a taccalonolide compound in an amount sufficient to inhibit the proliferation of said hyperproliferative cells, wherein said taccalonolide has the structure;

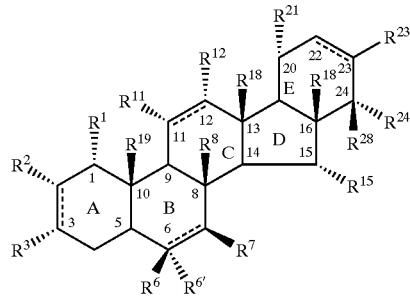

wherein:

$R^1$=hydroxy, lower alkoxy or acyloxy, $R^2$=OH, or $R^2$ and $R^3$ cooperate to form an epoxide at C-2/C-3, $R^3$=OH, or $R^3$ cooperates with $R^2$ to form an epoxide at C-2/C-3, $R^6$=OH, or a carbonyl oxygen if $R^{6'}$ is not present,
$R^{6'}$, when present, is H,
$R^7$=hydroxy, lower alkoxy or acyloxy,
$R^8$=H,
$R^{11}$=H, hydroxy, lower alkoxy or acyloxy,
$R^{12}$=hydroxy, loser alkoxy or acyloxy,
$R^{15}$=hydroxy, lower alkoxy or acyloxy,
$R^{16}$=H,
$R^{18}$=H or lower alkyl,
$R^{19}$=lower alkyl,
$R^{21}$=lower alkyl,
$R^{23}$=hydroxy, lower alkoxy or acyloxy,
$R^{24}$=hydroxy, lower alkoxy or acyloxy, and
$R^{28}$=lower alkyl;
wherein the dashed lines between C2/C3, C6/C7, C11/C12 and C22/23 represent optional double bonds at each position.

17. A method for alleviating a pathological condition caused by mammalian cells with drug-resistant phenotype, said method comprising contacting mammalian cells with drug resistant phenotype with a taccalonolide compound in an amount sufficient to alleviate said pathological condition, wherein said taccalonolide has the structure:

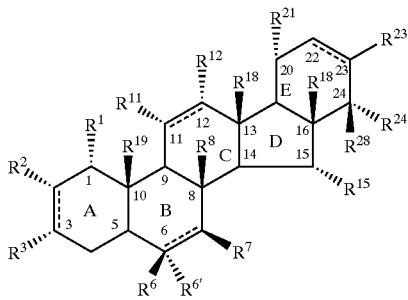

wherein:
$R^1$=hydroxy, lower alkoxy or acyloxy,
$R^2$=OH, or $R^2$ and $R^3$ cooperate to form an epoxide at C2/C-3,
$R^3$=OH, or $R^3$ cooperates with $R^2$ to form an epoxide et C2/C-3,
$R^6$=OH, or a carbonyl oxygen if $R^{6'}$ is not present,
$R^{6'}$, when present, is H,
$R^7$=hydroxy, lower alkoxy or acyloxy,
$R^8$=H,
$R^{11}$=H, hydroxy, lower alkoxy or acyloxy,
$R^{12}$=hydroxy, lower alkoxy or acyloxy,
$R^{15}$=hydroxy, lower alkoxy or acyloxy,
$R^{16}$=H,
$R^{18}$=H or lower alkyl,
$R^{19}$=lower alkyl,
$R^{21}$=lower alkyl,
$R^{23}$=hydroxy, lower alkoxy or acyloxy,
$R^{24}$=hydroxy, lower alkoxy or acyloxy, and
$R^{28}$=lower alkyl;
wherein the dashed lines between C2/C3, C6/C7, C11/C12 and C22/23 represent optional double bonds at each position.

18. A method of inhibiting the proliferation of a hyperproliferative mammalian cell having a multiple drug resistant phenotype, said method comprising contacting a hyperproliferative mammalian cell having a multiple drug resistant phenotype with an amount of a taccalonolide compound effective to disrupt the dynamic state of microtubule polymerization and depolymerization to arrest cell mitosis, thereby inhibiting the proliferation of the cell, wherein said taccalonolide has the structure;

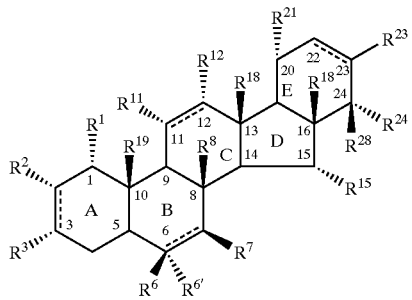

wherein:
$R^1$=hydroxy, lower alkoxy or acyloxy,
$R^2$=OH, or $R^2$ and $R^3$ cooperate to form an epoxide at C-2/C-3,
$R^3$=OH, Or $R^3$ cooperates with $R^2$ to form an epoxide at C-2/C-3,
$R^6$=OH, or a carbonyl oxygen if $R^{6'}$ is not present,
$R^{6'}$, when present, is H,
$R^7$=hydroxy, lower alkoxy or acyloxy,
$R^8$=H,
$R^{11}$=H, hydroxy, lower alkoxy or acyloxy,
$R^{12}$=hydroxy, lower alkoxy or acyloxy,
$R^{15}$=hydroxy, lower alkoxy or acyloxy,
$R^{16}$=H
$R^{18}$=H or lower alkyl,
$R^{19}$=lower alkyl,
$R^{21}$=lower alkyl,
$R^{23}$=hydroxy, lower alkoxy or acyloxy,
$R^{24}$=hydroxy, lower alkoxy or acyloxy, and
$R^{28}$=lower alkyl;
wherein the dashed lines between C2/C3, C6/C7, C11/C12 and C22/23 represent optional double bonds at each position.

19. A method according to claim 1, wherein said taccalonolide is selected from the group consisting of taccolonolide A, taccolonolide B, taccolonolide C and taccolonolide D.

* * * * *